United States Patent
Matji Tuduri et al.

(10) Patent No.: US 7,935,853 B2
(45) Date of Patent: May 3, 2011

(54) MICRONIZED COMPOSITION OF A 2,4-DISUBSTITUTED PHENOL DERIVATIVE

(75) Inventors: José Antonio Matji Tuduri, Madrid (ES); Juan Lopez Belmonte Pascual, Madrid (ES)

(73) Assignee: Bobelium S.L., Madrid (ES)

( * ) Notice: Subject to any disclaimer, the term of this patent is extended or adjusted under 35 U.S.C. 154(b) by 0 days.

(21) Appl. No.: 12/575,829

(22) Filed: Oct. 8, 2009

(65) Prior Publication Data

US 2010/0094063 A1    Apr. 15, 2010

(30) Foreign Application Priority Data

Oct. 9, 2008 (EP) .................................... 08380288

(51) Int. Cl.
*C07C 39/27* (2006.01)
*A61K 31/055* (2006.01)

(52) U.S. Cl. ......................... 568/775; 568/776; 514/731

(58) Field of Classification Search .................. None
See application file for complete search history.

(56) References Cited

U.S. PATENT DOCUMENTS

| 6,824,791 B2 * | 11/2004 | Mathiowitz et al. .......... 424/458 |
| 2005/0281739 A1 | 12/2005 | Gong et al. |
| 2008/0057129 A1 * | 3/2008 | Lerner et al. ................ 424/489 |

FOREIGN PATENT DOCUMENTS

WO    95/21610    8/1995

OTHER PUBLICATIONS

International European Search Report; EP 2 174 654; S. Schule; Mar. 2, 2009.

* cited by examiner

*Primary Examiner* — Brian J Davis
(74) *Attorney, Agent, or Firm* — Fish & Richardson P.C.

(57) ABSTRACT

A composition comprising a 2,4,-disubstituted phenol derivative in its micronized form and its use in the treatment of leukotriene-mediated diseases, gastrointestinal-inflammatory diseases or pulmonary fibrosis. More particularly, 2,4,6-triiodophenol can be used for the treatment of pulmonary fibrosis and arthritis.

9 Claims, 6 Drawing Sheets

MICRONIZED COMPOSITION OF A 2,4-DISUBSTITUTED PHENOL DERIVATIVE

CROSS-REFERENCE TO RELATED APPLICATION

Under 35 U.S.C. §119, this application claims the benefit of a foreign priority of European patent application 08380288.4, filed Oct. 9, 2008 the contents of which are hereby incorporated by reference in their entirety.

TECHNICAL FIELD

The present invention refers to a composition comprising a 2,4-disubstituted phenol derivative in its micronized form and its use in the treatment of leukotriene-mediated diseases, gastrointestinal-inflammatory diseases or pulmonary fibrosis. More particularly, the present invention refers to use of 2,4,6-triiodophenol for the treatment of pulmonary fibrosis and arthritis.

BACKGROUND

Certain derivative of 2,4-disubstituted phenols have been used for the preparation of drugs against leukotriene-mediated diseases, such as rheumatoid arthritis, ulcerative colitis, asthma, psoriasis and herpes, due to the powerful activity of said derivatives as inhibitors of the inducible isoform of nitric oxide synthase (iNOS) and as an inhibitor of the expression of the L-selectin adhesion molecule on the surface of the plasma membrane of the leukocytes, as described in PCT published application number WO 95/21610.

SUMMARY

The present disclosure refers to a micronized composition comprising 2,4,6-triiodophenol and its use in the treatment of leukotriene-mediated diseases, among which gastrointestinal-inflammatory diseases, arthritis or pulmonary fibrosis are included. This composition can provide certain pharmacokinetic, therapeutic and tolerability advantages in a multiple administration regime, in particular in maintaining a concentration range within an adequate therapeutic index.

The compound presents clear advantages, both pharmacokinetic as well as in efficacy and tolerability over the non-micronized compound. To demonstrate this, a Phase I clinical trial in healthy volunteers was carried out where doses of 240, 350 and 500 mg of the non-micronized compound were administered orally in a multiple administration dosing regime (see example 4). From this study it can be concluded that there is a greater accumulation of the compound than what corresponds to a lineal pharmacokinetic profile (see FIG. 9). This prevents the possibility of proposing a design that, after a multiple dose administration regime, allows the plasma concentration of the compound to be maintained within a desired range. However, the composition described solves this problem.

Therefore, a first feature refers to a composition comprising 2,4,6-triiodophenol of formula:

characterized in that the 2,4,6-triiodophenol in the composition is in its micronized form.

The micronization of the 2,4,6-triiodophenol was carried out by standardized methods which form part of the general common knowledge. In a preferred embodiment, the method results in a particle size less than to 20 microns and a water content less than to 1%. More preferably the method results in a particle size less than to 15 microns, in an even more preferably embodiment the average size is between 2 and 5 microns and a water content less than to 0.5%.

A second feature refers to the composition as described above for its use as a medicament. Preferably, for its use in the treatment of leukotriene-mediated diseases, among which gastrointestinal-inflammatory diseases and pulmonary fibrosis are included.

Wherein the leukotriene-mediated disease is selected from the list that comprises rheumatoid arthritis, osteoarthritis, spondylitis, juvenile arthritis, gout, coxoplanar dysplasia, arthrosis, discoespondylitis, bursitis, tendonitis or equine cauda, and the gastrointestinal-inflammatory leukotriene-mediated diseases are selected from the list that comprises chronic intestinal pathology, ulcerative colitis, Crohn's disease, gastritis, rectitis or lymphoplasmacitarial enteritis.

The composition described may optionally include any conventional ingredients for improving the physical properties, visual appearance or odor of a pharmaceutical composition.

The phrase "pharmaceutically acceptable" indicates that the substance or composition must be compatible chemically and/or toxicologically, with the other ingredients comprising a formulation, and/or the mammal being treated therewith.

The compositions and methods will be better understood by reference to the following examples, which illustrate but do not limit the compositions and methods described herein.

EXAMPLES OF EMBODIMENTS

Example 1

Determination of Inhibitory Activity Over 5-Lipoxygenase Ex-Vivo in Rat Whole Blood This example demonstrates the inhibitory activity of a micronized sample of 2,4,6-triiodophenol over the 5-lipoxygenase enzyme ex-vivo in rate whole blood, and compares its inhibitory activity with that of a non-micronized sample of the same substance.

In the example shown 3 groups of animals (rats) were used, with 6 rats in each group. The groups were;

1 group 1: control (vehicle)
2 group 2: treated with micronized test substance (10 mg/Kg)
3 group 3: treated with non-micronized test substance (10 mg/Kg)

The distribution of animals to each group was done in a randomized manner at the start of the study.

The test and reference substances were administered orally as a suspension in 0.25% carboximethylcellulose in a dosing volume of 4 ml/kg via an oral cannula.

Test substance administration was carried out once every 24 hours (09 h 00 min) for 5 consecutive days. On the 5$^{th}$ day a blood sample was obtained from each animal (1 mL) 1 hour after administration of the test and reference substances. Blood samples were obtained from the posterior (abdominal) vena cava in sterile syringes containing sodium citrate (4%) as an anticoagulant. Each blood sample was divided into two 0.5 ml aliquots (duplicates). A 1 hour time lapse after test substance administration was used before obtaining the blood samples as it was determined in preliminary studies that this is when there is a greater inhibition of leukotriene synthesis by the test substance.

Immediately after collection of the blood samples, the duplicated aliquots were incubated at 37° C. for 10 min. After this time, the aliquots were stimulated with calcium ionophore (30 μM, final concentration) for 30 min at 37° C. Once the incubation period was over the aliquots were centrifuged at 12.000 g for 2 minutes. The resulting plasma was separated and stored at −20° C. for its posterior analysis. In these samples the concentration of leukotriene B4 was determined by enzyme immunoassay (kit EIA; Amersham).

TABLE I

| Control | | Micronized | | Non-Micronized | |
|---|---|---|---|---|---|
| Sample code | LTB4 (ng/ml) | Sample Code | LTB4 (ng/ml) | Sample Code | LTB4 (ng/ml) |
| C1 | 10.102 | MI-1 | 4.583 | R-1 | 4.355 |
| C2 | 6.466 | MI-2 | 6.118 | R-2 | 4.905 |
| C3 | N/A | MI-3 | 4.602 | R-3 | 8.818 |
| C4 | 9.319 | MI-4 | 6.067 | R-4 | 9.682 |
| C5 | 7.599 | MI-5 | 6.549 | R-5 | 6.862 |
| C6 | 7.535 | MI-6 | 5.032 | R-6 | 4.355 |

| Group | LTB4 | | |
|---|---|---|---|
| Mean | (ng/ml) | s.e.m. | S.D. |
| Control | 8.204 | 0.659 | 1.473 |
| Micron | 5.492 | 0.350 | 0.857 |
| S. Ref. | 6.496 | 0.955 | 2.340 |

TABLE II

| Micronized | | Non-Micronized | |
|---|---|---|---|
| Sample code | LTB4 % inhib. | Sample code | LTB4 % inhib. |
| MI-1 | 44.140 | R-1 | 46.917 |
| MI-2 | 25.423 | R-2 | 40.210 |
| MI-3 | 43.902 | R-3 | −7.480 |
| MI-4 | 26.054 | R-4 | −18.013 |
| MI-5 | 20.176 | R-5 | 16.356 |
| MI-6 | 38.665 | R-6 | 46.917 |

| Group | LTB4 | | |
|---|---|---|---|
| Mean | % inhib. | s.e.m. | S.D. |
| Micron | 33.060 | 4.263 | 10.442 |
| S. Ref. | 20.818 | 11.643 | 28.520 |

Figure 1:
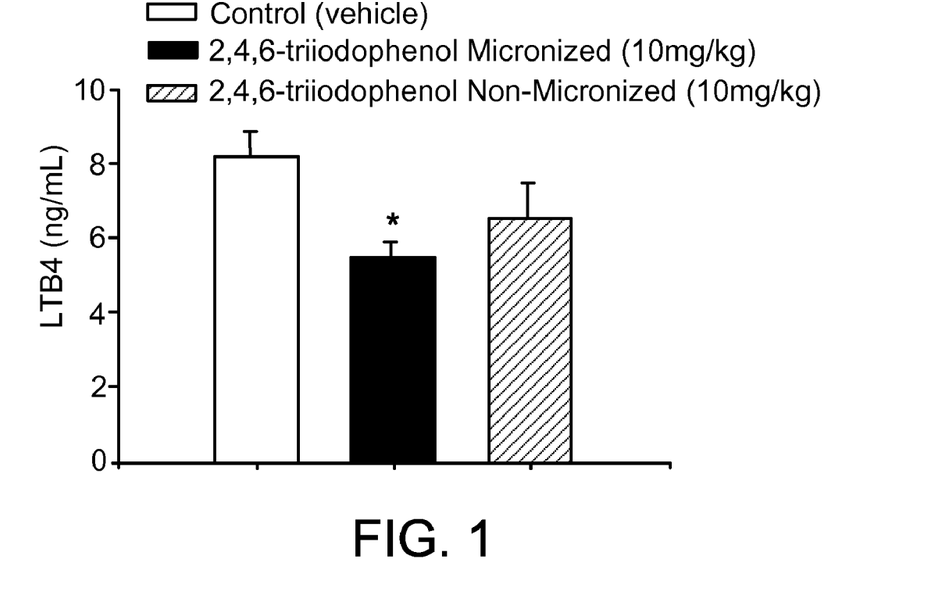
FIG. 1 is a comparison of ex-vivo inhibition of 5-lipoxygenase activity in rat whole blood by a micronized sample of 2,4,6-triiodophenol with that of a non-micronized sample of the same substance.

The results obtained show (Tables I, II and FIG. 1) that the micronized product, at a dose of 10 mg/kg inhibits, in a statistically significant manner (*P<0.05, ANOVA+Dunnett's test) leukotriene B$_4$ formation (LTB$_4$) by 5-lipoxygenase ex-vivo in rat whole blood stimulated with calcium ionophore after 5 days of oral treatment. Additionally, the degree of inhibition is superior to that obtained with the non-micronized product, and the variability of the results is also less than (less variability).

Example 2

Preliminary Study of Activity in a Model of Pulmonary Fibrosis Induced by Bleomycin in Mice This example demonstrates the ability of the micronized 2,4,6-triiodophenol to reduce the cellular infiltration observed in bronchoalveolar lavage fluid (as an indicator of tissue infiltration) that is characteristic of pulmonary fibrosis and that can be reproduced in a model of the disease induced in mice by a single intratracheal administration of bleomycin to mice.

Administration of bleomycin resulted in an increase of total cellularity of bronchoalveolar lavage fluid 21 days later. In particular there was an increase in the percentage of lymphocytes and neutrophils in the cell population from said lavages, and a decrease in the percentage of macrophages.

Similarly, bleomycin administration also resulted in a significative increase in the concentration of the pro-inflammatory chemokine CCL5 and TGFβ in bronchoalveolar lavage fluid after 21 days.

These are typical characteristics of pulmonary fibrosis in this animal model and are indicative of the severity of the disease and the inflammatory response in the lungs.

Oral administration of micronized 2,4,6-triiodophenol, at a dose of 10 mg/kg (twice per day), starting 7 days after bleomycin administration (therapeutic treatment, once there is an established pulmonary inflammation) resulted in a reduction of the bleomycin-induced increase in lymphocytes and neutrophil percentages in bronchoalveolar lavage fluid, and an increase in the percentage of macrophages towards the values observed in healthy control animals.

Similarly, treatment with the micronized compound also resulted in a very significant inhibition of the bleomycin-induced increase in the concentration of both CCL5 and TGFβ in bronchoalveolar lavage fluid.

These results demonstrate an anti-inflammatory activity of the micronized compound in a model of pulmonary fibrosis in the mouse.

In the study, female, young and healthy C57/BL6 mice were used, of approximately 9-10 weeks of age at the start of the experimental phase. The choice of C57/BL6 mice was because this is the most commonly used mouse strain in the pulmonary fibrosis model.

Three experimental groups were used in the study:

Group A: (positive control): Bleomycin+Vehicle (PBS) n=10

Group B: Bleomycin+2,4,6-triiodophenol micronized 10 mg/kg q.d. (every 12 hours) n=10

Group C: No treatment (healthy animals) n=1

Where n is the number of animals in each experimental group.

The test item was administered as a suspension in 0.25% methylcellulose (the vehicle). The positive control group received the vehicle.

Both the test item and the vehicle were administered orally in a volume of 5 ml/kg twice per day (q.d.) every 12 hours.

On day 0 pulmonary fibrosis was induced by intratracheal instillation of 0.075 units of bleomycin in 50 µl of sterile saline solution into the lungs of each animal. Immediately afterwards 150 µl of air were introduced intratracheally into each mouse to aid in the pulmonary distribution of the bleomycin.

On day 7 after bleomycin administration, treatment with the test item or vehicle was commenced by oral administration. Treatment was carried out twice per day (every 12 hours) and was continued for 15 days.

On day 21 after bleomycin administration a bronchoalveolar lavage was carried out on all animals. To this effect, mice were anaesthetized with sodium pentobarbital and the trachea of each animal was cannulated. Afterwards 1 ml of PBS at 37° C. was instilled into each lung and re-aspirated back with the use of a syringe. This process was repeated 5 times, each time collecting the aspirated liquid in a vial and combining the liquid obtained from the 5 lavages. The recovered volume of bronchoalveolar lavage was adjusted for all animals to 5 mls.

Once the bronchoalveolar lavage fluid had been obtained, a sample was taken in order to determine cellular viability by trypan blue exclusion. Additionally, a sample of lavage fluid was kept frozen (−20° C.) for subsequent determination of CCL5 and TGF-β concentration by ELISA.

The remaining bronchoalveolar lavage fluid was spun in a cytocentrifuge and stained (Diff-Quick) in order to carry out a differential cell count.

All animals were weighed on arrival at the laboratory and each day during the treatment phase of the experimental period until the end of the study.

For each animal cell viability in bronchoalveolar lavage fluid was determined by Trypan Blue exclusion, and a differential cell count was done by staining cytocentrifuged samples with Diff-Quick stain (this was done on a population of approximately 200 cells per sample). Additionally, the concentration of CCL5 and TGF-β were also determined in bronchoalveolar lavage fluid samples by the use of commercially available ELISA kits specific for mice chemokines from R&D Systems.

TABLE III

Differential Cell Count in Bronchoalveolar Lavage Fluid (%)

| Groups | Macrophages | | | Lymphocytes | | | Neutrophils | | |
|---|---|---|---|---|---|---|---|---|---|
| | Mean | S.D. | S.E.M. | Mean | S.D. | S.E.M. | Mean | S.D. | S.E.M. |
| A | 39.21 | 22.30 | 8.43 | 52.35 | 18.43 | 6.97 | 8.44 | 4.35 | 1.64 |
| B | 60.33 | 20.53 | 7.76 | 34.35 | 18.36 | 6.94 | 5.32 | 3.58 | 1.35 |
| CONTROL | 86.12 | | | 13.43 | | | 0.45 | | |

Figure 2:
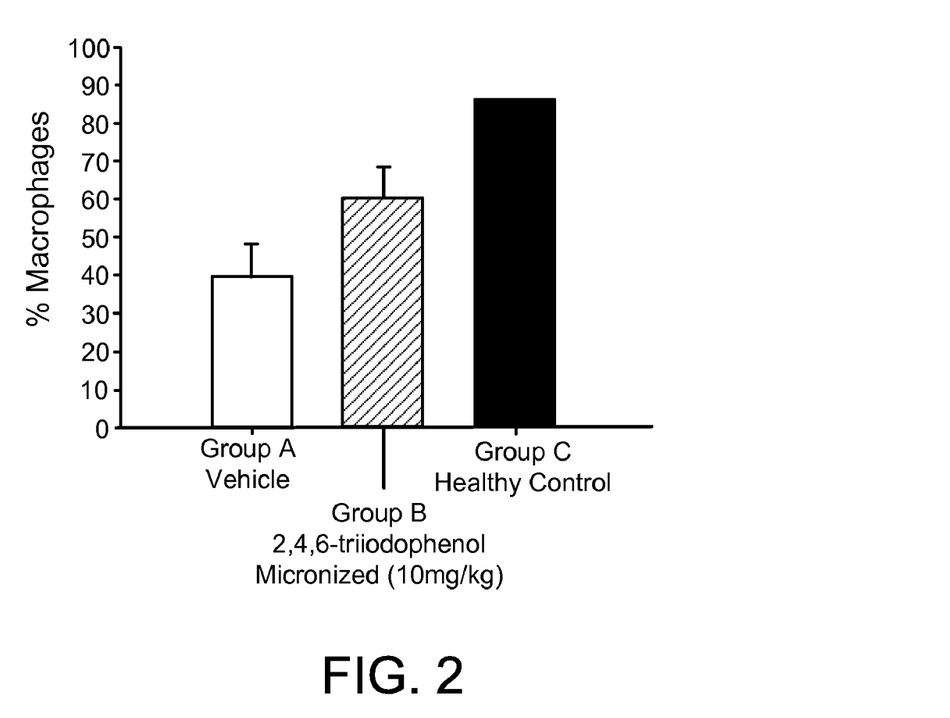
FIG. 2 is a differential count of macrophages in bronchoalveolar lavage fluid. Results are shown as the mean of 1 to 9 animals per group±the standard error of the mean (results expressed as the % of macrophages in the total cell count in lavage).
Figure 3:
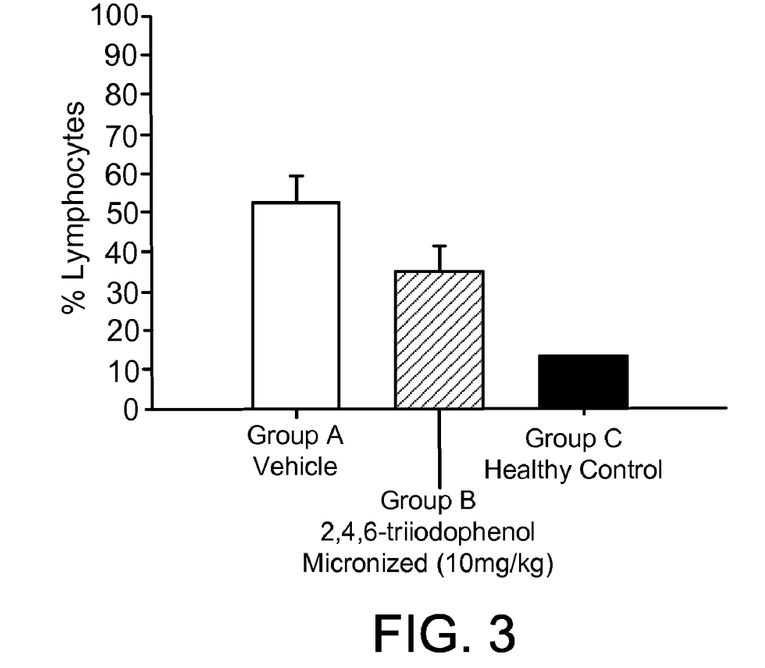
FIG. 3 is a differential count of lymphocytes in bronchoalveolar lavage fluid. Results are shown as the mean of 1 to 9 animals per group±the standard error of the mean (results expressed as the % of lymphocytes in the total cell count in lavage).
Figure 4:
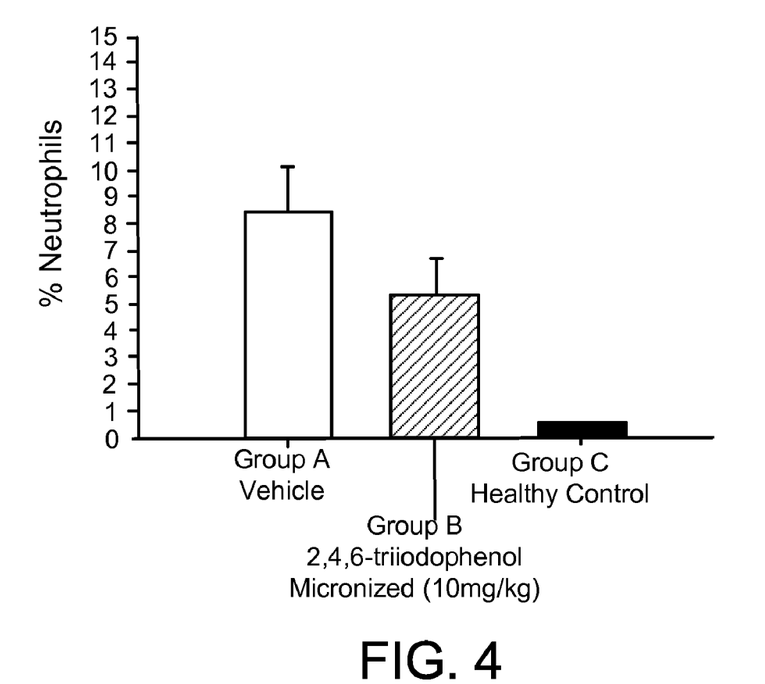
FIG. 4 is a differential count of neutrophils in bronchoalveolar lavage fluid. Results are shown as the mean of 1 to 9 animals per group±the standard error of the mean (results expressed as the % of neutrophils in the total cell count in lavage).

Table III shows the differential cell count of bronchoalveolar lavage fluid, expressed as the percentage of each type of cell from the total number of cells. The data are shown as the mean, standard deviation of the mean (S.D.) and standard error of the mean (S.E.M.) for each experimental group. This results are shown graphically in FIG. 2.

Figure 5:
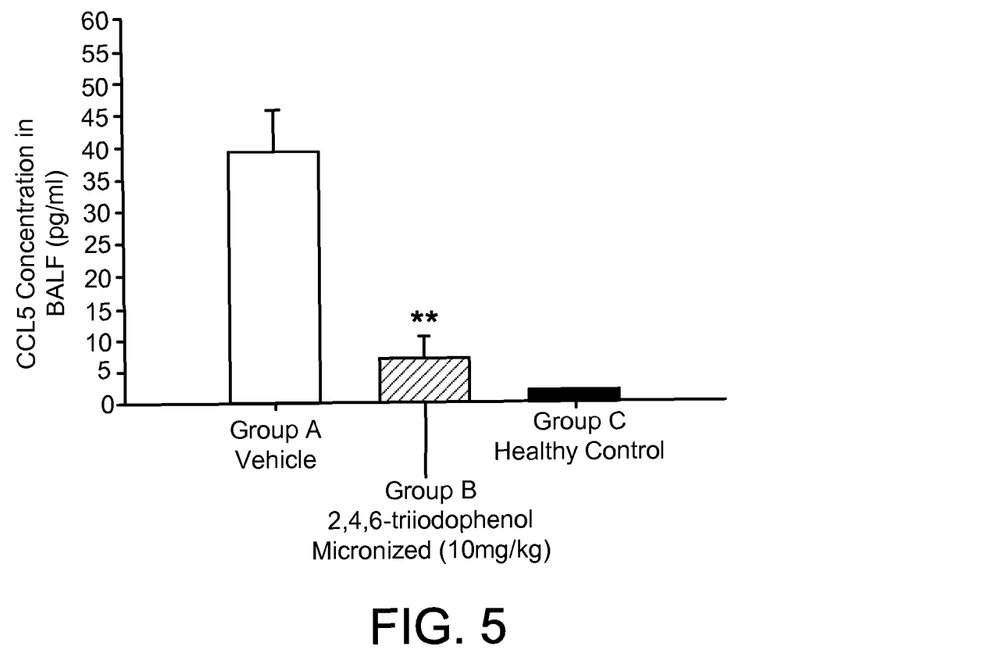
FIG. 5 is a CCL5 concentration in bronchoalveolar lavage fluid (BALF). Results are shown as the mean (n=1-9)±the Standard error of the mean. **P<0.01 vs. Group A (Student's t-test).

The concentration of CCL5 was determined in a sample of bronchoalveolar lavage fluid of all surviving animals from each experimental group on day 21. The results obtained are summarized in Table IV and depicted graphically in FIG. 5.

TABLE IV

Concentration of CCL5 in BALF.
CCL5 Concentration in BALF

| Group A | | Group B | | CONTROL |
|---|---|---|---|---|
| Animal | C (pg/ml) | Animal | C (pg/ml) | C (pg/ml) |
| A1 | 55.892 | B1 | 24.658 | |
| A2 | 13.734 | B2 | 3.426 | |
| A3 | 52.507 | B5 | 2.272 | |
| A4 | 58.353 | B7 | 1.887 | |
| A5 | 41.506 | B8 | 3.041 | |
| A7 | 27.351 | B9 | 6.426 | |
| A8 | 48.506 | | | |
| A9 | 16.196 | | | |
| Mean | 39.256 | Mean | 6.952 | 1.579 |
| S.D. | 17.859 | S.D. | 8.821 | |
| S.E.M. | 6.314 | S.E.M. | 3.334 | |

Results are shown as pg/ml of BALF.

The concentration of TGFβ1 was determined in a sample of bronchoalveolar lavage fluid of all surviving animals from each experimental group on day 21.

Figure 6:
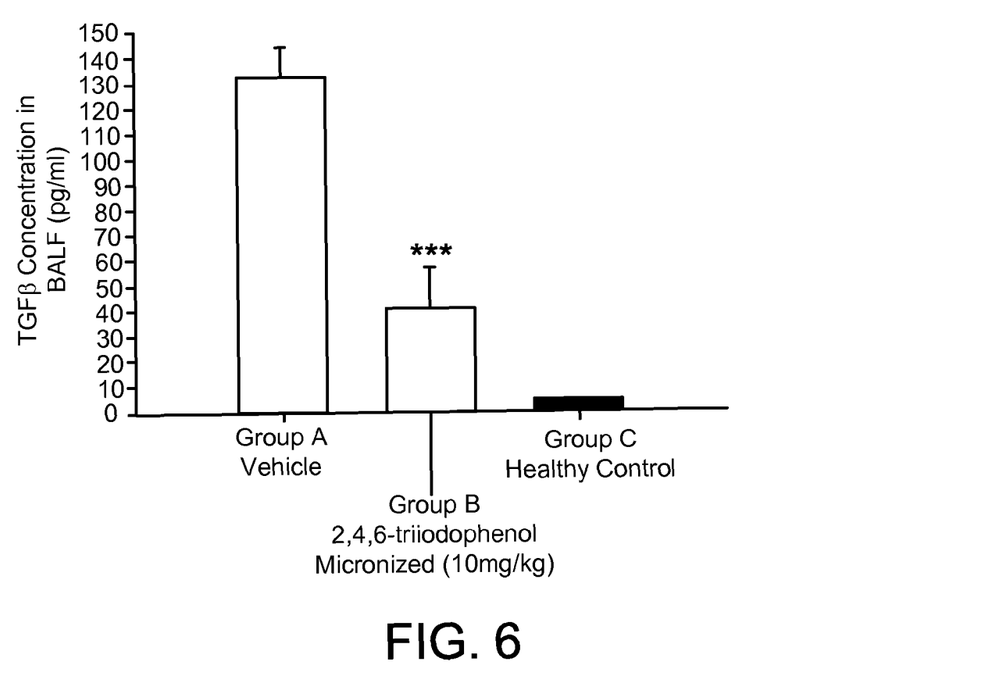
FIG. 6 is a TGFβ1 concentration in bronchoalveolar lavage fluid (BALF). Results are shown as the mean (n=1-9)±the Standard error of the mean. ***P<0.001 vs. Group A (Student's t-test).
Figure 7:
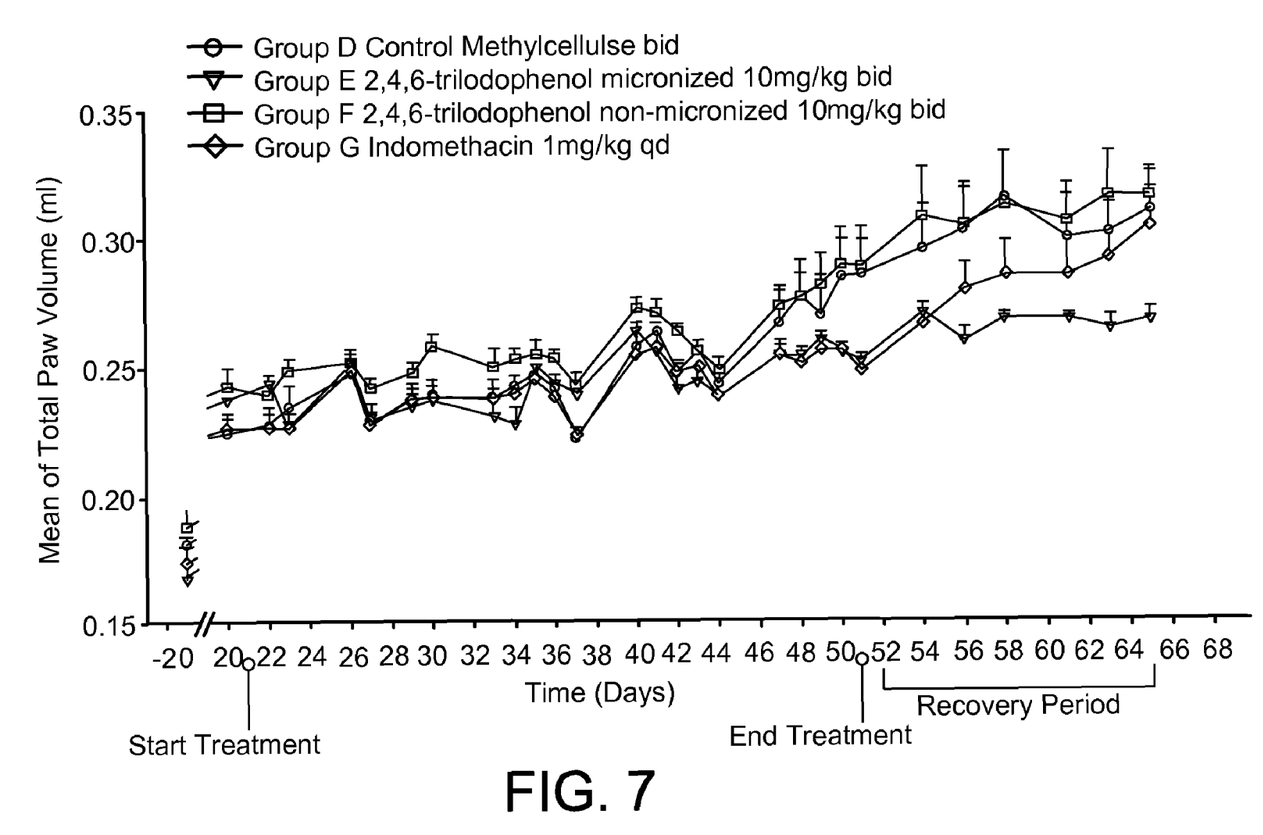
FIG. 7 is a change in total volume of hind paws of experimental groups D, E and F (administration B.I.D.). Results are shown as the mean (n=10)±the Standard error of the mean.
Figure 8:
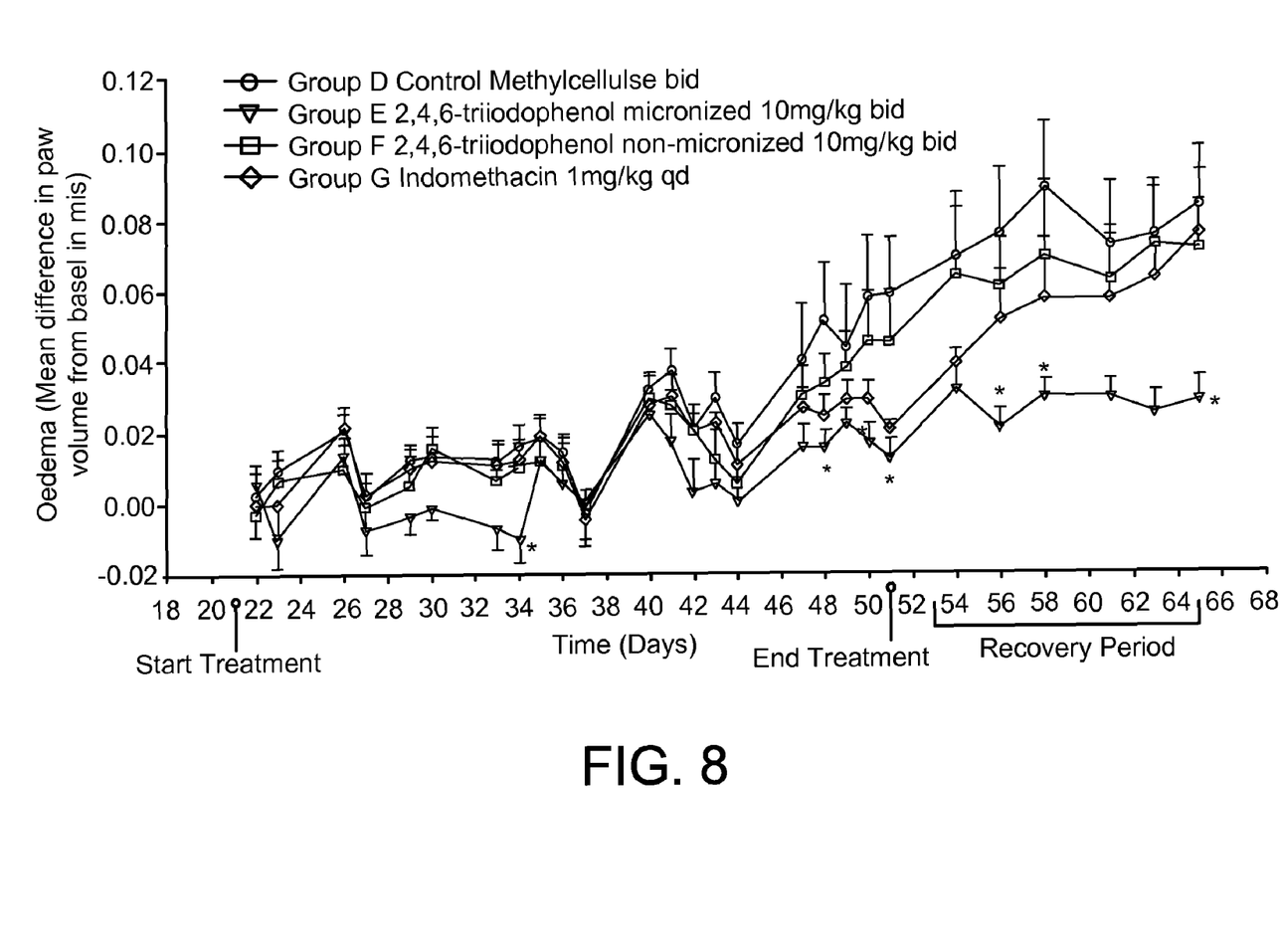
FIG. 8 is a oedema (difference in paw volume from basal values on day 20) shown as the sum of both hind paws for experimental groups D, E and F (administration B.I.D.) over the experimentation period. Results are shown as the mean (n=10)±the standard error of the mean.

The results obtained are summarized in Table V and depicted graphically in FIG. 6.

TABLE V

Concentration of TGFβ1 en BALF.
TGFβ Concentration in BALF

| Group A | | Group B | | CONTROL |
|---|---|---|---|---|
| Animal | C (pg/ml) | Animal | C (pg/ml) | C (pg/ml) |
| A1 | 140.912 | B1 | 121.586 | |
| A2 | 91.906 | B2 | 9.770 | |
| A3 | 146.434 | B4 | 74.651 | |
| A4 | 124.347 | B5 | 6.319 | |
| A5 | 136.771 | B7 | 8.389 | |
| A7 | 142.983 | B8 | 26.335 | |
| A8 | 190.608 | B9 | 38.069 | |
| A9 | 85.694 | | | |
| Mean | 132.457 | Mean | 40.731 | 3.558 |
| S.D. | 33.112 | S.D. | 42.995 | |
| S.E.M. | 11.707 | S.E.M. | 16.250 | |

Results are shown as pg/ml of BALF.

The statistical significance of the results was evaluated by use of the statistical package Graphpad Instat 3.

All comparisons were evaluated by the use of Student's t-test (two-way, unpaired data). Values of $P \leq 0.05$ were taken as significant.

Example 3

Anti-Inflammatory Activity in a Model of Arthritis Induced by Collagen Administration in Mice The aim of the study was to determine the anti-inflammatory activity of the test item in a model of arthritis induced by injection of type II collagen in the mouse (CIA) and to compare the activity of two different formulations: micronized and non-micronized.

Induction of arthritis was carried out by an initial exposure to type II bovine collagen by a subcutaneous injection at the base of the tail (induction phase).

After a recovery time of 21 days, animals received a booster injection and approximately 4-5 weeks after the first injection there was an immune response with arthritis appearing in the extremities in the majority of the cases.

Treatment of animals with the reference item Indomethacin (1 mg/kg Q.D) resulted in a significant anti-inflammatory response over the observed oedema (inflammation of the hind paws) in certain days during the study.

Treatment of the animals with the micronized formulation of the test item 2,4,6-triiodophenol 10 mg/kg BID, resulted in significant (P<0.05) reductions in the observed oedema on days 48, 50, 56, 58 and 65 (with percentage inhibitions versus the control group of 68.72±8.98, 70.56±9.88, 71.49±7.19, 66.29±5.13 y 64.95±7.58 respectively). Also a highly significant inhibition was observed on day 51 (77.59±9.08).

In contrast, treatment of the animals with the non-micronized formulation of the test item 2,4,6-triiodophenol 10 mg/kg BID, did not result in any significant inhibition of the hind paw oedema in any of the days of the experimental period.

As a conclusion, the results obtained in the present study demonstrate that the test item's anti-inflammatory activity varies depending on the pharmaceutical formulation being used (micronized and non-micronized), with the micronized form giving the best results.

Four experimental groups were used in the study with 10 animals in each group:
  Group D: Positive control: FCA+vehicle B.I.D.
  Group E: Micronized Test Item (Micro) 10 mg/kg B.I.D.
  Group F: Non-Micronized test item 10 mg/kg B.I.D.
  Group G: Reference item: Indomethacin 1 mg/kg Q.D.
  The dose administered to groups E and F was 10 mg/kg.
  The dose administered to group G was 1 mg/kg.
  The doses of the test and reference items were expressed as mg/Kg of compound administered to each animal.

The test and reference items were administered in a solution of methylcellulose (0.25%: vehicle).

The positive control group received the vehicle (methylcellulose 0.25%).

metilcelulosa 0.25% (vehículo).

The test and reference items, as well as the vehicle were administered orally at a dosing volume of 5 mls/kg.

The route of administration used was oral by use of an intragastric cannula.

On the day of start of the study each mouse was injected subcutaneously at the base of the tail with a first dose of 0.1 ml of an emulsion of bovine type II collagen (1 mg/mL) in Freund's Complete Adjuvant. Afterwards, on day 21 after this first injection, a second booster injection of type II collagen was administered to all animals. In this occasion the collagen suspension was done using Incomplete Freund's Adjuvant.

Coinciding with the second booster injection on day 21 treatment with the test or reference items was started to the corresponding animals.

Treatment with the test or reference items was carried out for 31 consecutive days (days 21-51 of the experimental period). Additionally, a recovery period was included at the end of the treatment period from day 52 to day 65 in order to evaluate the duration of any anti-inflammatory effect observed once dosing has been terminated.

The animals' hind paw volume was measured by plethysmometry one day before the 1st injection of collagen, again one day before the second (booster) collagen injection (basal values) and then daily after administration of test/reference item until the end of the study. During the recovery period at the end of the study, hind paw volume was measured three times per week.

The data obtained during the study was summarized as tables. Additionally the data was also represented graphically, depicting changes in total hind paw volume, as well as oedema (differences from basal (day 21) values).

TABLE VI

Total Hind Paw Volume (sum of both hind paws).
TOTAL HIND PAW VOLUME

| TIME (Day) | | Group D | Group E | Group F | Group G |
|---|---|---|---|---|---|
| 0 | Mean | 0.183 | 0.169 | 0.189 | 0.175 |
| | S.D. | 0.009 | 0.019 | 0.022 | 0.021 |
| | s.e.m. | 0.003 | 0.006 | 0.007 | 0.007 |
| 20 | Mean | 0.226 | 0.238 | 0.243 | 0.227 |
| | S.D. | 0.022 | 0.014 | 0.025 | 0.014 |
| | s.e.m. | 0.007 | 0.005 | 0.008 | 0.005 |
| 22 | Mean | 0.228 | 0.244 | 0.240 | 0.227 |
| | S.D. | 0.023 | 0.010 | 0.024 | 0.017 |
| | s.e.m. | 0.007 | 0.003 | 0.008 | 0.006 |
| 23 | Mean | 0.235 | 0.228 | 0.250 | 0.227 |
| | S.D. | 0.026 | 0.023 | 0.014 | 0.018 |
| | s.e.m. | 0.008 | 0.008 | 0.004 | 0.006 |
| 26 | Mean | 0.247 | 0.252 | 0.253 | 0.249 |
| | S.D. | 0.029 | 0.009 | 0.014 | 0.014 |
| | s.e.m. | 0.009 | 0.003 | 0.004 | 0.004 |
| 27 | Mean | 0.228 | 0.231 | 0.242 | 0.228 |

TABLE VI-continued

Total Hind Paw Volume (sum of both hind paws).
TOTAL HIND PAW VOLUME

| TIME (Day) | | Group D | Group E | Group F | Group G |
|---|---|---|---|---|---|
| | S.D. | 0.016 | 0.016 | 0.014 | 0.014 |
| | s.e.m. | 0.005 | 0.005 | 0.004 | 0.004 |
| 29 | Mean | 0.238 | 0.234 | 0.248 | 0.237 |
| | S.D. | 0.016 | 0.017 | 0.013 | 0.015 |
| | s.e.m. | 0.005 | 0.006 | 0.004 | 0.005 |
| 30 | Mean | 0.239 | 0.237 | 0.259 | 0.239 |
| | S.D. | 0.023 | 0.016 | 0.015 | 0.012 |
| | s.e.m. | 0.007 | 0.005 | 0.005 | 0.004 |
| 33 | Mean | 0.238 | 0.231 | 0.250 | 0.238 |
| | S.D. | 0.024 | 0.017 | 0.025 | 0.011 |
| | s.e.m. | 0.008 | 0.006 | 0.008 | 0.003 |
| 34 | Mean | 0.242 | 0.228 | 0.254 | 0.240 |
| | S.D. | 0.015 | 0.019 | 0.011 | 0.013 |
| | s.e.m. | 0.005 | 0.006 | 0.004 | 0.004 |
| 35 | Mean | 0.245 | 0.250 | 0.255 | 0.246 |
| | S.D. | 0.016 | 0.012 | 0.017 | 0.016 |
| | s.e.m. | 0.005 | 0.004 | 0.005 | 0.005 |
| 36 | Mean | 0.241 | 0.244 | 0.254 | 0.239 |
| | S.D. | 0.012 | 0.010 | 0.009 | 0.014 |
| | s.e.m. | 0.004 | 0.003 | 0.003 | 0.004 |
| 37 | Mean | 0.223 | 0.239 | 0.243 | 0.222 |
| | S.D. | 0.012 | 0.014 | 0.017 | 0.011 |
| | s.e.m. | 0.004 | 0.005 | 0.005 | 0.003 |
| 40 | Mean | 0.258 | 0.263 | 0.273 | 0.255 |
| | S.D. | 0.013 | 0.010 | 0.014 | 0.008 |
| | s.e.m. | 0.004 | 0.003 | 0.004 | 0.003 |
| 41 | Mean | 0.263 | 0.256 | 0.271 | 0.257 |
| | S.D. | 0.012 | 0.013 | 0.017 | 0.014 |
| | s.e.m. | 0.004 | 0.004 | 0.005 | 0.004 |
| 42 | Mean | 0.247 | 0.241 | 0.264 | 0.247 |
| | S.D. | 0.015 | 0.019 | 0.008 | 0.011 |
| | s.e.m. | 0.005 | 0.006 | 0.003 | 0.004 |
| 43 | Mean | 0.256 | 0.244 | 0.255 | 0.250 |
| | S.D. | 0.014 | 0.012 | 0.016 | 0.010 |
| | s.e.m. | 0.004 | 0.004 | 0.005 | 0.003 |
| 44 | Mean | 0.243 | 0.238 | 0.248 | 0.238 |
| | S.D. | 0.019 | 0.018 | 0.017 | 0.017 |
| | s.e.m. | 0.006 | 0.006 | 0.005 | 0.005 |
| 47 | Mean | 0.266 | 0.254 | 0.273 | 0.254 |
| | S.D. | 0.044 | 0.016 | 0.019 | 0.013 |
| | s.e.m. | 0.014 | 0.005 | 0.006 | 0.004 |
| 48 | Mean | 0.277 | 0.254 | 0.277 | 0.252 |
| | S.D. | 0.044 | 0.010 | 0.027 | 0.007 |
| | s.e.m. | 0.014 | 0.003 | 0.009 | 0.002 |
| 49 | Mean | 0.270 | 0.261 | 0.281 | 0.256 |
| | S.D. | 0.048 | 0.007 | 0.038 | 0.011 |
| | s.e.m. | 0.015 | 0.002 | 0.012 | 0.003 |
| 50 | Mean | 0.284 | 0.255 | 0.289 | 0.256 |
| | S.D. | 0.047 | 0.008 | 0.046 | 0.008 |
| | s.e.m. | 0.015 | 0.003 | 0.014 | 0.002 |
| 51 | Mean | 0.285 | 0.251 | 0.288 | 0.248 |
| | S.D. | 0.042 | 0.009 | 0.049 | 0.013 |
| | s.e.m. | 0.013 | 0.003 | 0.016 | 0.004 |
| 54 | Mean | 0.295 | 0.270 | 0.307 | 0.266 |
| | S.D. | 0.054 | 0.013 | 0.062 | 0.010 |
| | s.e.m. | 0.017 | 0.004 | 0.020 | 0.003 |
| 56 | Mean | 0.302 | 0.259 | 0.304 | 0.279 |
| | S.D. | 0.055 | 0.015 | 0.051 | 0.034 |
| | s.e.m. | 0.017 | 0.005 | 0.016 | 0.011 |
| 58 | Mean | 0.315 | 0.268 | 0.312 | 0.285 |
| | S.D. | 0.056 | 0.007 | 0.065 | 0.043 |
| | s.e.m. | 0.018 | 0.002 | 0.021 | 0.013 |
| 61 | Mean | 0.30 | 0.27 | 0.31 | 0.28 |
| | S.D. | 0.05 | 0.01 | 0.05 | 0.05 |
| | s.e.m. | 0.02 | 0.00 | 0.02 | 0.01 |
| 63 | Mean | 0.30 | 0.26 | 0.32 | 0.29 |
| | S.D. | 0.04 | 0.02 | 0.05 | 0.07 |
| | s.e.m. | 0.01 | 0.01 | 0.02 | 0.02 |
| 65 | Mean | 0.31 | 0.27 | 0.31 | 0.30 |
| | S.D. | 0.05 | 0.01 | 0.04 | 0.05 |
| | s.e.m. | 0.02 | 0.00 | 0.01 | 0.02 |

TABLE VII

Oedema (difference in paw volume from basal values on day 21) in both hind paws.
OEDEMA (difference to paw volume from basal day 21)

| TIME (Day) | | Group D | Group E | Group F | Group G |
|---|---|---|---|---|---|
| 0 | Mean | | | | |
| | S.D. | | | | |
| | s.e.m. | | | | |
| 20 | Mean | | | | |
| | S.D. | | | | |
| | s.e.m. | | | | |
| 22 | Mean | 0.003 | 0.006 | −0.003 | 0.000 |
| | S.D. | 0.029 | 0.010 | 0.019 | 0.008 |
| | s.e.m. | 0.009 | 0.003 | 0.006 | 0.003 |
| 23 | Mean | 0.010 | −0.010 | 0.007 | 0.000 |
| | S.D. | 0.011 | 0.025 | 0.027 | 0.026 |
| | s.e.m. | 0.003 | 0.008 | 0.009 | 0.008 |
| 26 | Mean | 0.022 | 0.014 | 0.010 | 0.022 |
| | S.D. | 0.014 | 0.012 | 0.029 | 0.017 |
| | s.e.m. | 0.005 | 0.004 | 0.009 | 0.005 |
| 27 | Mean | 0.003 | −0.007 | −0.001 | 0.001 |
| | S.D. | 0.022 | 0.022 | 0.019 | 0.018 |
| | s.e.m. | 0.007 | 0.007 | 0.006 | 0.006 |
| 29 | Mean | 0.013 | −0.003 | 0.006 | 0.011 |
| | S.D. | 0.014 | 0.016 | 0.026 | 0.016 |
| | s.e.m. | 0.004 | 0.005 | 0.008 | 0.005 |
| 30 | Mean | 0.014 | −0.001 | 0.016 | 0.012 |
| | S.D. | 0.020 | 0.012 | 0.020 | 0.014 |
| | s.e.m. | 0.006 | 0.004 | 0.006 | 0.004 |
| 33 | Mean | 0.012 | −0.007 | 0.007 | 0.012 |
| | S.D. | 0.020 | 0.020 | 0.010 | 0.018 |
| | s.e.m. | 0.006 | 0.007 | 0.003 | 0.006 |
| 34 | Mean | 0.017 | −0.010 | 0.011 | 0.013 |
| | S.D. | 0.020 | 0.021 | 0.020 | 0.017 |
| | s.e.m. | 0.006 | 0.007 | 0.006 | 0.005 |
| 35 | Mean | 0.020 | 0.012 | 0.013 | 0.020 |
| | S.D. | 0.017 | 0.017 | 0.018 | 0.018 |
| | s.e.m. | 0.005 | 0.006 | 0.006 | 0.006 |
| 36 | Mean | 0.015 | 0.006 | 0.011 | 0.012 |
| | S.D. | 0.015 | 0.013 | 0.021 | 0.023 |
| | s.e.m. | 0.005 | 0.004 | 0.007 | 0.007 |
| 37 | Mean | −0.002 | 0.001 | 0.000 | −0.005 |
| | S.D. | 0.023 | 0.011 | 0.032 | 0.022 |
| | s.e.m. | 0.007 | 0.004 | 0.010 | 0.007 |
| 40 | Mean | 0.032 | 0.026 | 0.030 | 0.028 |
| | S.D. | 0.015 | 0.014 | 0.019 | 0.015 |
| | s.e.m. | 0.005 | 0.005 | 0.006 | 0.005 |
| 41 | Mean | 0.038 | 0.018 | 0.028 | 0.031 |
| | S.D. | 0.020 | 0.025 | 0.013 | 0.020 |
| | s.e.m. | 0.006 | 0.008 | 0.004 | 0.006 |
| 42 | Mean | 0.022 | 0.003 | 0.021 | 0.021 |
| | S.D. | 0.020 | 0.030 | 0.022 | 0.016 |
| | s.e.m. | 0.006 | 0.010 | 0.007 | 0.005 |
| 43 | Mean | 0.030 | 0.006 | 0.013 | 0.023 |
| | S.D. | 0.022 | 0.022 | 0.027 | 0.009 |
| | s.e.m. | 0.007 | 0.007 | 0.009 | 0.003 |
| 44 | Mean | 0.017 | 0.001 | 0.006 | 0.011 |
| | S.D. | 0.019 | 0.022 | 0.020 | 0.018 |
| | s.e.m. | 0.006 | 0.007 | 0.006 | 0.006 |
| 47 | Mean | 0.041 | 0.016 | 0.031 | 0.028 |
| | S.D. | 0.051 | 0.020 | 0.027 | 0.016 |
| | s.e.m. | 0.016 | 0.007 | 0.008 | 0.005 |
| 48 | Mean | 0.052 | 0.016 | 0.034 | 0.025 |
| | S.D. | 0.052 | 0.014 | 0.026 | 0.018 |
| | s.e.m. | 0.016 | 0.005 | 0.008 | 0.006 |
| 49 | Mean | 0.044 | 0.023 | 0.039 | 0.030 |
| | S.D. | 0.056 | 0.013 | 0.032 | 0.016 |
| | s.e.m. | 0.018 | 0.004 | 0.010 | 0.005 |
| 50 | Mean | 0.059 | 0.017 | 0.046 | 0.030 |
| | S.D. | 0.054 | 0.017 | 0.044 | 0.016 |
| | s.e.m. | 0.017 | 0.006 | 0.014 | 0.005 |
| 51 | Mean | 0.060 | 0.013 | 0.046 | 0.021 |
| | S.D. | 0.050 | 0.016 | 0.045 | 0.008 |
| | s.e.m. | 0.016 | 0.005 | 0.014 | 0.002 |
| 54 | Mean | 0.070 | 0.032 | 0.065 | 0.040 |
| | S.D. | 0.059 | 0.021 | 0.061 | 0.013 |
| | s.e.m. | 0.019 | 0.007 | 0.019 | 0.004 |
| 56 | Mean | 0.076 | 0.022 | 0.062 | 0.052 |
| | S.D. | 0.060 | 0.016 | 0.044 | 0.045 |

TABLE VII-continued

Oedema (difference in paw volume from basal values on day 21) in both hind paws.
OEDEMA (difference to paw volume from basal day 21)

| TIME (Day) | | Group D | Group E | Group F | Group G |
|---|---|---|---|---|---|
| | s.e.m. | 0.019 | 0.005 | 0.014 | 0.014 |
| 58 | Mean | 0.089 | 0.030 | 0.070 | 0.058 |
| | S.D. | 0.060 | 0.014 | 0.067 | 0.052 |
| | s.e.m. | 0.019 | 0.005 | 0.021 | 0.017 |
| 61 | Mean | 0.073 | 0.030 | 0.063 | 0.058 |
| | S.D. | 0.058 | 0.016 | 0.046 | 0.057 |
| | s.e.m. | 0.018 | 0.005 | 0.015 | 0.018 |
| 63 | Mean | 0.076 | 0.026 | 0.073 | 0.064 |
| | S.D. | 0.049 | 0.019 | 0.058 | 0.079 |
| | s.e.m. | 0.015 | 0.006 | 0.018 | 0.025 |
| 65 | Mean | 0.084 | 0.029 | 0.072 | 0.076 |
| | S.D. | 0.054 | 0.019 | 0.042 | 0.058 |
| | s.e.m. | 0.017 | 0.006 | 0.013 | 0.018 |

Example 4

Population Pharmacokinetic Analysis of 2,4,6-Triiodophenol in its Non-Micronized Form in Healthy Volunteers after Multiple Administration The aim of the study was to carry out a population pharmacokinetic analysis of 2,4,6-triiodophenol in its non-micronized form in plasma samples obtained from healthy volunteers.

Many factors can lead to a discontinuation in the development of a new drug. While approximately 50% of the failures are caused by a lack of efficacy, adverse effects, or animal toxicity, poor pharmacokinetic characteristics are a very important issue during drug development as they are responsible for almost 40% of failures. Slow absorption rate, low bioavailability, poor tissue penetration, non-linear behavior, presence of toxic metabolites, or high variability are examples of limited pharmacokinetic properties, and to find out if they can be overcome with the currently available tools is a challenge. In addition to pharmaceutical technology which is used routinely to improve absorption and distribution properties, data modeling helps in the case of non-linear kinetics to identify the cause(s) by discriminating between rival hypothesis, the onset and offset, and the clinical impact of the non-linearity.

2,4,6-triiodophenol is a potent leukotriene B4 ($LTB_4$) synthesis inhibitor that is currently under clinical development. The exact mechanism of action of 2,4,6-triiodophenol is not completely understood but it is known that the inhibition of the enzyme 5-lipoxygenase is involved. Results obtained from the first phase I clinical trial—where a single dose was administered orally to healthy volunteers—showed that 2,4,6-triiodophenol had very good safety and tolerability profiles (from 6 mg to 1200 mg). In addition, a predictable and dose-independent (at least in the range from 240 to 700 mg) pharmacokinetic behavior could be described with a first-order rate of absorption model and a-one-compartment disposition model. A direct and non-linear ($E_{MAX}$ type) relationship between plasma concentrations and $LTB_4$ synthesis inhibition with a value of $IC_{50}$ (the level of drug in plasma eliciting half of maximal $LTB_4$ synthesis inhibition) of 16.6 µg/ml was also found.

In a second phase I study, giving 2,4,6-triiodophenol in a multiple-dosing regime, the drug showed a totally unexpected increase in the area under the concentration vs. time curve (AUC), a phenomenon that might compromise the drug development process.

Thirty-two volunteers participated in this study. All participants gave their written informed consent after a full explanation of the trial protocol and prior to their enrolment. Approval was obtained from the ethics committee of the Hospital de la Santa Creu i Sant Pau and the Spanish Drug Regulatory Agency. The study was conducted in accordance with the Declaration of Helsinki and Tokyo as well as to GCP. Healthy male volunteers aged between 18 and 45 years and a Quetelet index within the normal range were admitted to the study.

Volunteers were not eligible for the study if medical examination or laboratory tests differed significantly from normal clinical values, or in cases of known gastrointestinal, hepatic, renal, respiratory, cardiovascular, metabolic, immunological, hormonal, central nervous system or psychiatric disorders. Volunteers with chronic or relevant acute infections, history of allergy/hypersensitivity to drugs including NSAIDS, smoking of more than 10 cigarettes per day, drinking of more than 45 g of alcohol per day, or drug dependency were excluded. Intake of any other drug in the two weeks prior to the study was not allowed. Lastly, volunteers who had undergone surgery in the last 6 months or those who had participated in another study with an investigation drug within the two months preceding the study were also excluded.

Study design. This was a randomized, double-blind, placebo-controlled, parallel single and multiple dose phase I study. The goal was to evaluate the pharmacokinetics and tolerability of three different oral doses of 2,4,6-triiodophenol. After a one-day screening phase performed within the four weeks prior to the study, the volunteers were randomized into four groups of eight subjects each, receiving 240, 350 or 500 mg of 2,4,6-triiodophenol or placebo orally with 125 mL of plain water after a 10 h fast. Each volunteer received seven doses: a single dose was given on day 1, then 2,4,6-triiodophenol or placebo were administered once daily from day 8 to 13. Volunteers arrived at the Pharmacology Research Unit at 7 AM on days 1 and 13 and remained there for 24 h. The participants were served standard meals for breakfast, lunch and dinner. From days 2 to 12, volunteers arrived at 7 AM and left the clinic after a pre-dose blood sampling (days 2 to 12), and intake of the next dose (days 8 to 12).

Sample collection and analytical determination: Blood samples (3 mL) were taken from a heparinized catheter implanted in a forearm vein at the following times: (i) pre-dose, 2, 4, 4.5, 5, 5.5, 6, 12, 24, 48, 72, 96, 120, 144 h after the single oral administration, (ii) pre-dose at days 8 to 12, and (iii), pre dose, 2, 4, 4.5, 5, 5.5, 6, 12, 24, 48, 72, 96, 120, and 144 after the last administered dose (day 13). These samples were collected in heparinized tubes and centrifuged (3500 r.p.m) at room temperature for 15 minutes. Plasma was then stored at −40° C. until analysis.

Concentrations of 2,4,6-triiodophenol in plasma were analyzed by a high-performance liquid chromatography (HPLC) method.

Data analysis: All pharmacokinetic data were analyzed simultaneously under the non-linear mixed effects modeling approach using the First Order Conditional Estimation method with the INTERACTION option implemented in the software NONMEM version V (Beal and Sheiner, 1992).

Disposition characteristics of 2,4,6-triiodophenol in the body were determined by fitting mono and multi- (two-, or three-) compartment models to the data. To describe drug input, models assuming either a first or zero-order rate of absorption, or a mixture of the two, were tested. The presence of a lag time in the absorption process was also investigated.

A preliminary exploratory analysis was done by simulating the typical pharmacokinetic profiles after single and multiple 240, 350, and 500 mg dose regimens based on the pharmacokinetic model and model parameter estimates obtained from the first phase I study, where 2,4,6-triiodophenol was given to healthy volunteers in a single dose ranging from 6 to 1200 mg.

Figure 9:
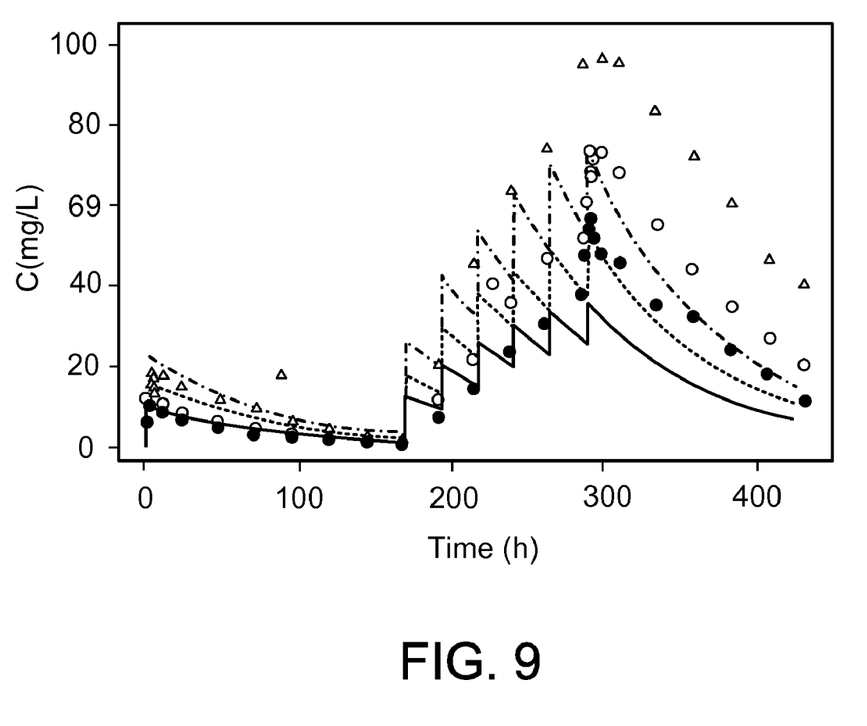
FIG. 9 is a mean observed concentration profiles and typical predicted population values obtained from a lineal pharmacokinetic model (lines) as a function of time; 240 mg (dots, continuous line), 350 mg (circles, dots and dashes), 500 mg (triangles, dashes).

FIG. 9 shows the results from this simulation exercise. It is clear that the model previously established behaves reasonably well after the administration of a single dose, however, observations are clearly under-predicted during the multiple dose treatment. Two parameters can influence AUC, bioavailability (F) and drug clearance (CL); in addition, CL affects the half-life of the drug. Both of them can also be modified by a change in the intrinsic enzymatic activity ($CL_{INT}$), among other factors.

What is claimed is:

1. A composition comprising 2,4,6-triiodophenol in micronized form in a particle size lower than 20 microns and the water content is lower than 1%.

2. A method for the treatment of a leukotriene-mediated disease in a subject, the method comprising:
   administering to the subject a therapeutically effective amount of a composition comprising 2,4,6-triiodophenol in micronized form in a particle size lower than 20 microns and the water content is lower than 1%.

3. The composition according to claim 1 where the particle size ranges from 2 to 5 microns and the water content is lower than 0.5%.

4. The method of claim 2 for the treatment of a leukotriene-mediated disease in a subject, the method comprising:
   administering, to the subject, a therapeutically effective amount of a composition comprising 2,4,6-triiodophenol in micronized form in a particle size that ranges from 2 to 5 microns and the water content is lower than 0.5%.

5. The method of claim 2, wherein the leukotriene-mediated disease is selected from the group consisting of rheumatoid arthritis, osteoarthritis, spondylitis, juvenile arthritis, gout coxoplanar dysplasia, arthrosis, discoespondylitis, bursitis, tendonitis, equine cauda, chronic intestinal pathology, ulcerative colitis, Crohn's disease, gastritis, rectitis, lymphoplasmacitarial enteritis, and pulmonary fibrosis.

6. The method of claim 4, wherein the leukotriene-mediated disease is selected from the group consisting of rheumatoid arthritis, osteoarthritis, spondylitis, juvenile arthritis, gout coxoplanar dysplasia, arthrosis, discoespondylitis, bursitis, tendonitis, equine cauda, chronic intestinal pathology, ulcerative colitis, Crohn's disease, gastritis, rectitis, lymphoplasmacitarial enteritis, and pulmonary fibrosis.

7. A method for reducing leukotriene levels in a subject in need thereof, the method comprising administering to the subject a therapeutically effective amount of a composition comprising 2,4,6-triiodophenol in micronized form in a particle size lower than 20 microns and the water content is lower than 1%.

8. The method of claim 7, comprising administering to the subject a therapeutically effective amount of a composition comprising 2,4,6-triiodophenol in micronized form in a particle size that ranges from 2 to 5 microns and the water content is lower than 0.5%.

9. The method of claim 7, wherein the subject has a disease selected from the group consisting of rheumatoid arthritis, osteoarthritis, spondylitis, juvenile arthritis, gout coxoplanar dysplasia, arthrosis, discoespondylitis, bursitis, tendonitis, equine cauda, chronic intestinal pathology, ulcerative colitis, Crohn's disease, gastritis, rectitis, lymphoplasmacitarial enteritis, and pulmonary fibrosis.

* * * * *